United States Patent
Orubor et al.

(10) Patent No.: US 8,097,241 B2
(45) Date of Patent: Jan. 17, 2012

(54) FORMULATION AND METHOD FOR TREATING ANIMAL WASTE

(76) Inventors: Lawrence Orubor, Calgary (CA); Ken Battle, Shamong, NJ (US); Roman Bielski, Coopersburg, PA (US)

( * ) Notice: Subject to any disclaimer, the term of this patent is extended or adjusted under 35 U.S.C. 154(b) by 871 days.

(21) Appl. No.: 12/062,346

(22) Filed: Apr. 3, 2008

(65) Prior Publication Data

US 2009/0047232 A1 Feb. 19, 2009

Related U.S. Application Data

(60) Provisional application No. 60/922,107, filed on Apr. 6, 2007.

(51) Int. Cl.
*A61L 11/00* (2006.01)
*A61K 38/47* (2006.01)
*A61K 38/48* (2006.01)
*A61P 31/00* (2006.01)

(52) U.S. Cl. .................. 424/76.6; 424/94.61; 424/94.63
(58) Field of Classification Search ........................ None
See application file for complete search history.

(56) References Cited

U.S. PATENT DOCUMENTS

| | | | | |
|---|---|---|---|---|
| 5,602,092 A | * | 2/1997 | Repinec et al. | 510/434 |
| 6,564,813 B1 | * | 5/2003 | Lengling et al. | 134/22.1 |
| 2006/0228323 A1 | | 10/2006 | Novelle et al. | |
| 2009/0047232 A1 | * | 2/2009 | Orubor et al. | 424/76.6 |

* cited by examiner

*Primary Examiner* — Shanon A Foley
(74) *Attorney, Agent, or Firm* — Maxey Law Offices, PLLC; Stephen Lewellyn

(57) ABSTRACT

The invention is directed to a formulation and method for treating solid waste from animals. The formulation comprises a surfactant having antimicrobial activity, preferably a cationic surfactant, and a solvent, preferably water. The preferred cationic surfactant is a quaternary ammonium compound. The formulation may further include one or more of acids, bases, enzymes, oxidizing agents, foamants, colorants, and/or fragrances. The formulation is prepared as a concentrate composition for use with a suitable diluent, such as water. The diluted composition is applied to the waste as a pressurized jet of fluid, such as using a sprayer attached to a garden hose. The result is that the solid waste is substantially sanitized, disintegrated and/or deodorized.

12 Claims, No Drawings

FORMULATION AND METHOD FOR TREATING ANIMAL WASTE

CROSS REFERENCE TO RELATED APPLICATIONS

This application claims the benefit of priority of U.S. Provisional Patent Application No. 60/922,107, filed Apr. 6, 2007, which is incorporated herein by reference in its entirety.

FIELD OF THE INVENTION

The present invention relates generally to the treatment of animal waste. More particularly, the present invention relates to the use of surfactant in a formulation and method for sanitizing, disintegrating and/or deodorizing animal waste.

BACKGROUND OF THE INVENTION

Animal waste, particularly raw fecal material, poses a number of potential problems to people (and other animals) that live, work or recreate in the vicinity of the waste. The problems include, but are not limited to, risk of infection by pathogens in the raw waste material, inhalation of obnoxious odours, and contamination of soil, water and food products grown in the vicinity of the raw waste material. The enormous volume of uncontrolled animal waste produced each year has a significant impact on the health of the population as well as the environment. In addition to the potential health risks, the presence and accumulation of animal waste in places such as backyards, public parks and recreational grounds is a general nuisance.

Animal waste is composed of both organic and inorganic matter. Organic matter includes proteins, polysaccharides, mucus and many microorganisms, including pathogens. In certain cases, animal waste contains infectious pathogens that can cause disease in humans. Infectious diseases that can be transmitted directly from animals to humans are termed zoonotic diseases. The risk of human infection depends on the resilience of the pathogen, the duration and nature of contact with the waste material and continuing contamination of the site. Persons at highest risk of infection from pathogens in raw animal waste include immuno-compromised individuals and children. Also at risk are individuals who come into frequent contact with animal waste, such as pet owners, gardeners and farmers. The hazards posed by zoonotic pathogens present in raw fecal material can be reduced with proper treatment and/or disposal of animal waste.

Exemplary zoonotic pathogens that may be present in raw animal waste include, but are not limited to, bacteria, such as *Escherichia coli* O157:H7, *Salmonella* and *Campylobacter jejuni*, and protozoa, such as *giardia duodenalis, Cryptosporidium parvum* and *Toxoplasma gondii*. The use of antibiotics and the like in formulations for treatment of animal waste is undesirable for many reasons, including high cost and the promotion of microbial resistance.

For the typical pet owner, cleaning up and disposing of pet waste is one of the biggest inconveniences of owning a pet. Disposal of pet waste in plastic bags and the like is detrimental to the environment, as are harsh chemical treatments of raw waste material. Composting of pet waste, while more environmentally friendly, is cumbersome and unpleasant. Furthermore, since most pet owners do not compost pet waste correctly, it is generally discouraged for public health reasons since it can promote the growth of pathogens.

On a somewhat larger scale, golf course operators and caretakers of various recreational grounds must contend with droppings from migratory and non-migratory birds and wildlife. Proper disposal of large amounts of animal waste can be extremely burdensome, not to mention unpleasant.

Public safety, cost and the environment must be taken into account when considering chemical treatment options. Many of the currently available animal waste treatment and disposal methods are uneconomical, toxic and environmentally unfriendly.

The industrial facilities and treatment methods utilized in the farming industry are simply not practical for use by pet owners, recreational groundskeepers and the like, especially in cities. Various attempts at improving methods of treatment of animal waste have been made on an industrial scale, for example, in providing holding ponds or lagoons for water and/or bacterial decomposition, or by burning the solid refuse. However, these methods have not been entirely satisfactory and are impractical for use on less than an industrial scale.

Attempts have also been made to control the odour associated with animal fecal material. Such formulations are disclosed in United States Patent Application 2006/0228323, published Oct. 12, 2006. This application discloses a formulation containing an amphoteric surfactant for removing malodours from animal waste. When sprayed or fogged, the formulation forms a chemical complex with the odorous gas molecules thereby eliminating the unwanted odours. The formulation may be used to treat solid waste but only to the extent that the solid waste contains gas or liquid phase within it. It does not treat solid waste itself nor does it sanitize or disintegrate the solid waste. The solid waste remains after use of this amphoteric formulation.

It is, therefore, desirable to provide improved formulations and methods for treating animal waste that are effective, economical, practical, safe, and environmentally friendly. It is also desirable to provide a formulation and method of sanitizing, disintegrating and/or deodorizing animal waste.

SUMMARY OF THE INVENTION

It is an object of the present invention to obviate or mitigate at least one disadvantage of previous formulations or methods for treating animal waste. In particular, it is desirable to provide an economical and environmentally friendly formulation and method for sanitizing, disintegrating and/or deodorizing animal waste, such as pet and wildlife waste.

In one aspect of the present invention, there is provided a formulation for treating solid waste from animals, the formulation comprising a surfactant and a suitable solvent, preferably an aqueous solvent such as water. The surfactant may be a cationic, anionic, amphoteric, zwitterionic, non-ionic or other surfactant. Preferably, the surfactant is a cationic surfactant. More preferably, the cationic surfactant is a quaternary ammonium compound. The quaternary ammonium compound is preferably a quaternary ammonium salt, such as benzyltrimethylammonium chloride, cocamidopropyl PG-dimonium chloride phosphate or stearyldimoniumhydroxypropyl laurylglucosides chloride.

The formulation may also include one or more of acids, bases, enzymes (such as proteases or amylases), sanitizers, foamants, fragrances, redox reagents and/or colorants. Other additives commonly found in disinfectants and cleansers may also be added.

The formulation is preferably prepared as a concentrate composition for use with a suitable diluent. The formulation is preferably applied to the animal waste in diluted form to sanitize, disintegrate and/or deodorize the waste.

In one embodiment, the concentrate composition for treating solid waste from animals comprises from about 0.5-50.0% surfactant, from about 0.0-3.0% enzyme, from about 0.0-5.0% acid, from about 0.0-5.0% colourant, from about 0.0-5.0% foamant and from about 0.0-5.0% oxidizing agent; the remainder being a suitable solvent.

In a further aspect of the present invention, there is provided a method of applying the formulation to solid waste from animals, the preferred method comprising diluting a concentrate composition with a suitable diluent and spraying the diluted composition as a pressurized jet of fluid onto the waste to break down the waste.

DETAILED DESCRIPTION

The present invention generally provides a formulation and method for sanitizing, disintegrating and/or deodorizing animal waste. The formulation is preferably prepared as a concentrate composition and is diluted at the time of, or prior to, application to the animal waste.

The formulation and method of the present invention are particularly useful for sanitizing animal waste on a non-industrial scale since the formulations and methods are practical, economical, safe and environmentally friendly. By "animal waste" is meant raw fecal material, such as from wild, domesticated or companion animals.

By "non-industrial" scale is meant a scale where dedicated waste management facilities are not necessarily required or available. The formulations and methods of the present invention are thus particularly useful for sanitizing animal waste deposited, for example, in backyards, public parks, animal shelters, kennels, small farms, zoos or recreational facilities, such as golf courses. As a skilled person will appreciate, certain modifications could easily be made to scale-up the invention for use on an industrial scale.

The formulation of the invention comprises a surfactant or combination of surfactants for effecting one or more of sanitizing, disintegrating and deodorizing animal waste. The term surfactant refers to any number of surface active agents, which preferentially orient toward an interface. Classes of surfactants include non-Ionic surfactants, anionic surfactants, cationic surfactants, amphoteric surfactants, zwitterionic surfactants and combinations thereof. The surfactant preferably has antimicrobial activity. The antimicrobial activity may be bactericidal or bacteristatic depending on the particular formulation.

Preferably, the surfactants used in the present invention are cationic surfactants having antimicrobial activity. Cationic surfactants were found to provide the most effective antimicrobial action compared to other types of surfactants in treating animal waste. Cationic surfactants demonstrated significantly improved anti-bacterial effect and were found to be the most effective in disintegrating the fecal material itself. These surfactants also reduced the color of the waste, thereby enhancing the feeling that the waste was being disintegrated.

Suitable cationic surfactants include, but are not limited to, alkyl ammonium salts, quaternary ammonium compounds, quaternary phosphonium salts quaternary arsonium salts, tertiary sulfonium salts and tertiary selenonium salts.

A quaternary ammonium compound is analogous to an ammonium salt molecule wherein all four hydrogen atoms have been substituted with organic radicals. In general, when one of these radicals is a primary alkyl of about 8 to 18 carbon atoms chain length, and the others are only about 1 to 3 carbon atoms, the compound will be reasonably water soluble, surface active and strongly biocidal. If two or more of the substituent radicals are higher alkyls then the compound retains its cationic nature but becomes less water soluble and less biocidal.

Where quaternary ammonium salts are used, the immonium salts are considered to be particularly effective as antimicrobials or sanitizing agents. Quaternary ammonium compounds with no or low level of branching are considered to be the most environmentally friendly. In instances where the surfactant is a quaternary ammonium salt, the associated anion is preferably an inorganic anion. A halide (Cl, Br or I) is particularly preferred.

Exemplary quaternary ammonium compounds include, but are not limited to, benzyltrimethylammonium chloride, Colas Lipid C (cocamidopropyl PG-dimonium chloride phosphate), Suga®Quat S-1210 and Suga®Quat S-1218 (both stearyidimoniumhydroxypropyl laurylglucosides chloride).

In one embodiment, the surfactant is Cola®Lipid C, a coconut-derived phospholipid Comprised predominantly of diester and triester phosphatides with multiple chain groups, available from Colonial Chemical, Inc. (South Pittsburg, Tenn.). This surfactant provided significantly better antimicrobial activity than a simple quaternary ammonium salt such as benzyltrimethylammonium chloride.

Cola®Lipid C is a cationic surfactant having the structure:

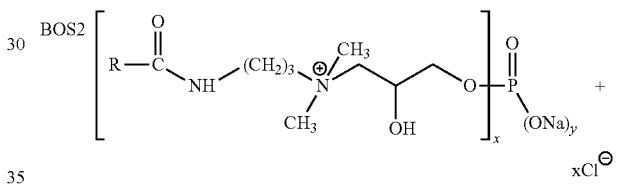

wherein R represents cocoamidopropyl ($C_{15}H_{31}CONH$—$(CH_2)_3$—) and x+y=3.

In certain embodiments where a cationic surfactant is used, it is preferable that the formulation has an acidic pH, i.e. below about 7. In general, cationic surfactants are more stable in an acidic pH.

Anionic surfactants are also useful in the context of the present invention, with significant antimicrobial effect. Anionic surfactants suitable for use in accordance with the present invention include, but are not limited to, sodium dodecyl sulfate (SDS) and sodium dodecylbenzene sulfonate.

In certain embodiments where an anionic surfactant is used, it is preferable that the formulation has a basic pH, i.e. above about 7. In general, anionic surfactants are not stable at low pH.

It is considered within the ordinary ability of the person skilled in the art having regard to the teachings of the present invention to determine the optimal pH of the formulation.

Non-ionic surfactants are also useful in the present invention. While they were found to be suitable for use in accordance with the present invention, they provided less antimicrobial effect than the anionic surfactants. Suitable non-ionic surfactants include, but are not limited to, Tween™ 80 (polysorbate 80), Tween™ 20 (polysorbate 20), Triton™ X-100 (octoxynol), BRIJ 35™ (polyoxyethyleneglycol dodecyl ether) and BRIJ 58™ (polyoxyethylene 20 cetyl ether).

The surfactant is dispersed or dissolved in a suitable carrier or solvent, preferably an aqueous carrier or solvent, such as water.

The formulation may comprise additional optional ingredients, including but not limited to, enzymes for breaking down organic matter, foamants, colourants, fragrances, stabilizers, emulsifiers, acids, bases, redox reagents and/or buffers. Other additives commonly used in sanitizers and cleansers may also be added.

The concentration of surfactant or combination of surfactants in the treatment formulation depends on the structure and antimicrobial activity of the individual surfactants. A desired amount of surfactant is an amount effective for sanitizing, disintegrating and/or deodorizing a sample of animal waste. Typically, the concentration of surfactant or combination of surfactants can range from about 0.5% to about 50% (w/w), more preferably from about 5% to about 50%, most preferably from about 15% to about 25%, in the concentrate composition.

One or more enzymes may optionally be added to the formulation to aid in degrading carbonaceous material present in the animal waste. For example, proteases or amylases may be added to the formulation to aid in digesting proteins or polysaccharides, respectively.

Enzymes also aid in decomposing microorganisms present in the waste, thereby enhancing the sanitizing effect of the formulation. Furthermore, destruction of odour-causing bacteria in the waste improves the odour of the waste and enhances the feeling of sanitization.

In one embodiment, enzymes are present in the formulation in an amount up to about 3% in the concentrate composition.

A protease may be present in the formulation in a range from 0.1% to about 10.0%, preferably 0.1% to about 5.0%, more preferably from about 0.1% to about 1.0%, in the concentrate composition. An exemplary protease preparation is Alcalase™ 3.0T, commercially available from Novozymes North America, Inc (Franklinton, N.C.). In the formulation exemplified in Table 3, the concentration of protease is 0.8%.

An amylase may be present in the formulation in a range from 0.1% to about 10.0%, preferably 0.1% to about 5.0%, more preferably from about 0.1% to about 1.0%, in the concentrate composition. An exemplary amylase preparation is Termamyl™ T, commercially available from Novozymes North America, Inc (Franklinton, N.C.). In the formulation exemplified in Table 3, the concentration of amylase is 0.2%.

In determining the optimal pH of the formulation, an acidic pH both inhibited the growth of bacteria present in the waste and assisted in neutralizing odour. Thus, while a basic or neutral pH is permissible in accordance with the present invention, an acidic pH, i.e. pH less than about 7, is preferred when cationic surfactants such as Cola®Lipid C are employed.

Where a cationic surfactant is used in the formulation of the present invention, the antimicrobial activity of the surfactant is enhanced in an acidic environment. An acid may optionally be added to the formulation to enhance the antimicrobial activity of the particular surfactant, particularly where a cationic surfactant is used. By way of example, addition of citric acid in the formulation exemplified in Table 3 significantly enhanced the antimicrobial activity of Cola®Lipid C compared to the same formulation without citric acid.

Other exemplary acids include, but are not limited to, acetic acid, propionic acid, oxalic acid and lactic acid.

The acid may be present in the formulation in a range from about 0.1% to about 10.0%, preferably 0.1% to about 5.0%, more preferably from about 0.1% to about 1.0% in the concentrate composition. In the formulation exemplified in Table 3, the concentration of citric acid is 0.15%.

One option in the prior art to minimize the malodor of feces is to apply specific enzymes or microorganisms. However, the action of bacteria or relevant enzymes is not very fast in neutralizing odors. Some existing enzyme-based products promise fast results in 2 to 12 hours, which timeframe is generally not considered to be "fast".

In the present invention, one option to reduce malodor was to take advantage of the basic or acidic character of malodorous components of feces and to use pH to reduce malodor. The malodor components of feces and urine derive almost exclusively from protein fermentation and can be divided into five categories, which are: ammonia in feces and urine, phenols and indoles in feces and urine, branched-chain fatty acids in feces, amines in feces, and volatile sulfur-containing compounds in feces. The compounds can be made non-odorous if they are transformed into non-volatile products. In general, the higher the molecular weight of a compound, the higher its boiling point and the less volatile it is. Compounds that are ionic are generally not volatile. Furthermore, compounds capable of the formation of hydrogen bonds will be of much lower volatility. In order for such compounds to become vapors they must overcome the forces of hydrogen bonds in addition to other forces.

Amines exhibit basic properties and include the malodorous amines potentially present in dog feces, such as putrescine and cadaverine, and indoles including skatole. Ammonia, amines (such as putrescine, cadaverine, spermidine), and indoles (such as skatole) react with acid to form relevant, non-volatile (ionic) salts. Amines can be oxidized to nitroso or nitro compounds, amine oxides and hydroxylamines, depending on the oxidizing agent and whether the amine is primary, secondary or tertiary.

Phenols, hydrogen sulfide, thiols, and carboxylic acids exhibit an acidic character. Many of these acidic compounds are malodorous components of feces. An increase in pH by reaction with a base transforms some phenols (such as p-cresol), branched-chain carboxylic acids (such as isobutyric, valeric, and isovaleric) and hydrogen sulfide and thiols (mercaptans) into relevant, non-volatile salts. For example, some phenols can be oxidized to quinones. However, by far, the most important oxidation in the context of odor is the oxidation of sulfur in sulfur-containing compounds to sulfur-oxygen bonds to produce higher boiling, hydrogen bond-forming (for example, with water), and water-soluble products. Thiols can be oxidized to non-volatile sulfonic acids, sulfides can be oxidized to sulfoxides and sulfones. Additionally, thiols can be oxidized with mild oxidants to disulfides (hydrogen sulfide can be oxidized with hydrogen peroxide to elemental sulfur).

Based on the above and without being bound by any particular theory, it is thought that destruction of amines and ammonia from urea compounds in the waste is enhanced in an acidic environment, i.e. pH below 7, thereby reducing odour caused by these compounds. In basic conditions, i.e. pH above 7, it is thought that thiols (i.e. mercaptans) are transformed into non-volatile salts thereby reducing odour.

One embodiment of the formulation uses an acidic pH (for example, pH about 2.0-6.5, about 3.0-6.0, about 4.0-5.0, or about 4.0), to remove amines while destroying the acidic malodor components by oxidation.

Another embodiment of the formulation uses a basic pH (for example pH about 7.5-11.0, about 8.0-10.0, about 9.0-10.0 or about 9.0), to address phenols, hydrogen sulfide, thiols, and/or carboxylic acids while destroying the acidic malodor components by oxidation.

Unfortunately, an increase or decrease in pH does not significantly affect malodorous sulfides (thioethers such as dimethylsulfide) and low molecular weight disulfides. Thus, while it was hoped to achieve fast removal of most malodorous compounds by decreasing pH, this gave only partial success. It was found that addition of an oxidizing agent, such as sodium perborate trihydrate or the like, to the formulation significantly reduced malodours in the feces. Without being bound by any particular theory, it is believed that odours derived from thioethers (sulfides) and disulfides, which cannot be addressed by employing acidic or basic pH, are addressed in the presence of the oxidizing agent.

Aqueous solutions of oxidizing agents, such as sodium perborate and metachloroperbenzoic acid (MCPBA), destroy the malodor very effectively. It is believed that this is due to sulfur atoms being oxidized to sulfoxides and/or sulfones.

Many oxidizing agents are known to execute some or all of the above oxidations. They include, but are not limited to, hydrogen peroxide (ex. in water or in acetic acid), sodium perborate, benzoyl peroxide, di-sodium phosphate, potassium permanganate, air/oxygen, dimethyldioxirane, peracids such as peracetic and peroxytrifluoroacetic, t-butyl hydroperoxide, sodium chlorite, sodium hypochlorite, potassium hydrogen persulfate, sodium persulfate, sodium percarbonate among others.

Preferred oxidizing agents for use in the formulation of the present invention are those that are least harmful to humans and animals, such as hydrogen peroxide, sodium perborate, sodium persulfate and sodium percarbonate.

Sodium perborate is preferred in one embodiment of the formulation of the present invention since it has been shown to execute most of the oxidation reactions of interest. The inventors have also demonstrated that it effectively minimizes the malodor of feces. However, there is a potential concern with the environmental impact of boron compounds and thus certain caution must be exercised when using boron compounds. The inventors have shown that most oxidants are effective as components of the inventive formulation, even when they act indirectly by releasing hydrogen peroxide.

The oxidizing agent may be present in the formulation in any suitable amount, for example, an amount from about 0.01% to about 5%, more preferably from about 0.1% to about 0.5% in the concentrate composition. In the formulation exemplified in Table 3, the concentration of oxidant is 0.3%.

In one embodiment, the formulation comprises 0.3% sodium percarbonate with a formulation pH of about 9. In another embodiment, the formulation comprises 0.3% sodium persulfate at a formulation pH of about 9.

In an alternative embodiment, an aqueous solution comprising hydrogen peroxide at about 0.1%-0.5%, preferably about 0.25%, at a formulation pH of about 4 to about 5, is employed. Hydrogen peroxide slowly decomposes but this is inhibited in acidic solution.

Foamants generally give a user an enhanced feeling that the formulation is actually "working". Foamants suitable for use in accordance with the present invention include, but are not limited to, Cola®Mate SS40 (disodium cocamido-MIPA suifosuccinate), Cola®Mate. DSLS and Cola®Lux Cao-35. Foamants may be present in the formulation in any suitable amount, for example, an amount from about 0.01% to about 5%, more preferrably from about 0.1% to about 1% in the concentrate composition. In the formulation exemplified in Table 3, the concentration of foamant is 0.5%.

Colorants may be used to give the formulation a pleasant appearance. Exemplary colorants are those selected from the Orcoterge™ line of tints, which are specialty dyes specifically selected for applications to detergents, chemical blends; and coatings, commercially available from Organic Dyestuffs Corporation (East Providence, R.I.). For example, Orcoterge™ Brilliant green AN-PH is used in the embodiment of the formulation shown in Table 3. Colorants may be present in the formulation in any suitable amount, for example, an amount from about 0.01% to about 5%, more preferably from about 0.01% to about 0.1% in the concentrate composition. In the formulation exemplified in Table 3, the concentration of colourant is 0.01%.

TABLE 1

Exemplary general Formulation For Treating Animal Waste (Concentrate Composition)

| CATEGORY | FUNCTION | PERCENT (%) |
|---|---|---|
| Surfactant | Antimicrobial, helps disintegrate the material | 0.5-50.0 |
| Enzymes | Digest organic matter | 0.0-3.0 |
| Acid | Antimicrobial, maintains pH required for other ingredients | 0.0-5.0 |
| Colourant | Gives color, no functionality | 0.0-5.0 |
| Foamant | The visualize detergent action | 0.0-5.0 |
| Oxidizing agent | Forms sulfur-oxygen bonds, for example transforms sulfides into sulfoxides and sulfones. | 0.0-5.0 |
| Solvent | | make up to 100% |

TABLE 2

Exemplary Formulation For Treating Animal Waste (Concentrate Composition)

| CATEGORY | INGREDIENT (exemplary) | FUNCTION | PERCENT (%) |
|---|---|---|---|
| Surfactant (ex. cationic) | Cola ® Lipid C | Antimicrobial, to help disintegrate the material | 15-25 |
| Enzyme (ex. protease) | Alcalase ™ 3.0T | Hydrolyses proteins | 0.1-1.0 |
| Enzyme (ex. amylase) | Termamyl ™ T | Hydrolyses most polysaccharides | 0.1-1.0 |
| Acid | Citric Acid | Antimicrobial, to maintain pH required for other ingredients | 0.1-0.2 |
| Colourant | Orcoterge ™ Brilliant green AN-PH | Gives green color, no functionality | 0.01-1 |
| Foamant | Cola ®Mate SS-40 | The visualize detergent action | 0.01-1 |
| Oxidizing agent | Sodium Perborate tetrahydrate | To transform sulfur compounds into non-volatile, water soluble products | 0.1-0.5 |
| Solvent | Water | | 70.3-84.58 |

TABLE 3

Embodiment of Formulation For Treating Animal Waste (Concentrate Composition)

| CATEGORY | INGREDIENT | FUNCTION | PERCENT (%) |
|---|---|---|---|
| Surfactant (cationic) | Cola ® Lipid C | Antimicrobial, to help disintegrate the material | 19.5 |

TABLE 3-continued

Embodiment of Formulation For Treating
Animal Waste (Concentrate Composition)

| CATEGORY | INGREDIENT | FUNCTION | PERCENT (%) |
|---|---|---|---|
| Enzyme | Alcalase 3.0T | Protease; Hydrolyses proteins | 0.8 |
| Enzyme | Termamyl T | Amylase; Hydrolyses most polysaccharides | 0.2 |
| Acid | Citric Acid | Antimicrobial, maintains pH required for other ingredients | 0.15 |
| Colourant | Orcoterge ™ Brilliant green AN-PH | Gives green color, no functionality | 0.01 |
| Foamant | Cola ®Mate SS-40 | The visualize detergent action | 0.5 |
| Oxidant | Sodium Perborate Tetrahydrate | To transform sulfur compounds into non-volatile, water soluble products | 0.3 |
| Solvent | Water | | 78.54 |

The formulation is preferably prepared as a concentrate composition. The concentrate composition may be applied directly to the animal waste but is preferably diluted at the time of, or just prior to, application to the animal waste. The concentrate composition is diluted with a suitable diluent, preferably water, for example, at a ratio of about 1:10 to about 1:200 when the waste is to be treated.

In one embodiment, the concentrate composition is prepared by first thoroughly dissolving a colourant in a selected quantity of carrier or solvent, preferably water. The surfactant, or combination of surfactants, and foamants are then added gently, with non-vigorous mixing to minimize formation of foam. Enzyme, oxidizing agent, and other optional ingredients are added, as desired, and gently mixed. It is advantageous to add enzymes dissolved in a small amount of water or other solvent. Finally, water or other suitable solvent is added carefully to bring the solution up to the required final mass.

The formulation is preferably applied by spraying or blasting the waste with the diluted formulation. For example, the concentrate composition can be diluted and applied to the animal waste using a spray bottle. In a preferred embodiment, the formulation is applied using a sprayer attached to a garden hose or the like, or a specialized device or machine having a means for providing a pressurized jet of fluid, to dilute the concentrate composition during, or just prior to, applying the treatment.

In one particular embodiment, the formulation is used in conjunction with the waste disintegrator described in U.S. Patent Application 60/810,764, filed Jun. 2, 2006, which is incorporated herein by reference. Generally, a sprayer, for providing the concentrate composition, is attached to a hose, such as a garden hose or other device for providing a pressurized jet of fluid. This is where the dilution step occurs. The resultant jet of fluid includes the formulation of the present invention in diluted form, and is applied at pressure to break up the solid waste. This pressurized application increases the disintegration of the solid waste and increases the surface area over which the surfactant and other active ingredients in the formulation can act on the waste.

The surfactant breaks down organic matter and destroys mucus, polysaccharides and the cell walls of microorganisms present in the waste. It also breaks up aggregates of microorganisms, thereby increasing access to the individual microorganisms to enhance microbial destruction. Although the surfactant will not sterilize the solid waste, it does significantly reduce the pathogens and sanitize it. Another advantage of this method of application is that disintegration and dilution allow the waste to readily soak into the ground or flow to a drain in the street to thereby dispose of the waste.

Example 1

The Effect of Various Additives on the Lowering of Animal Waste Bio-Burden

Materials and devices were as follows:
1. Dog waste collected at the local "Animals in Distress" facility (note: the specimen was refrigerated and replenished every 4 weeks)
2. Homogenizer
3. Sterile Erlenmeyer flasks
4. Vortex
5. Eppendorf pipetter
6. Graduated cylinder
7. Sterile pipette tips
8. Sterile test vials
9. Solid bacterial medium on Petri dishes (agar plates)
10. Deionized water (freshly boiled and cooled to the room temp)
11. Balance The Protocol was as follows:
1. A specific amount of a dog waste weighed with the accuracy of 1 mg (usually between 3 and 7 g) was transferred into the sterilized homogenizer. In a set of experiments performed on a given day the mass of all the samples were the same within 20.0 mg.
2. All the required additives were weighed out using the same balance and introduced into a specific amount of deionized, freshly boiled (but cooled to room temperature) water (usually between 50.0 g and 100.0 g) in the sterilized Erlenmeyer flask.
3. Next, the aqueous solution of additives was transformed into the homogenizer.
4. The mixture was mixed at low (18,000 RPM) for a specific amount of time (usually 30 seconds).
5. The resulting suspension was transferred to the sterilized Erlenmeyer flask and gradually diluted 10 times in several subsequent dilution steps. Initially, 5.0 mL of the non-diluted solution was added to 45.0 mL of deionized, freshly boiled water. The Eppendorf pipettes were used for further dilutions and in each case 0.110 mL of the previous sample after vortex was added to 0.900 mL of deionized, freshly boiled water in a sterile vial. Usually, 6 or 7 dilutions were performed. In every set of experiments one sample consisted of the feces and water only. All the results were measured against this sample.
6. After all the dilutions were finished, 100 microliters of each diluted sample was spread (sterile tip) onto a Petri dish with agar solid medium (kept in the refrigerator and removed from the refrigerator about 6 hours prior to experiments). Then, all the Petri dishes were turned upside down for about 20 minutes and returned to the original position after the agar was clearly dried.
7. The dishes were left for 48 or 72 hours at ambient temperature.
8. Next, each sample was counted to determine the number of CFUs (colony forming units).

Table 4 below shows results from a typical experiment.

TABLE 4

Results from a typical experiment:

| | Waste (g) | Water (mL) | Detergent (g) | Acid or base (g) | Enzyme Protease (Aldrich) | pH | Foam formed | Suspension color |
|---|---|---|---|---|---|---|---|---|
| 1 | 3.951 | 75.0 | none | none | 0 | 7 | none | dark |
| 2 | 4.095 | 75.0 | Cola Lipid 1.050 | Acetic 0.35 Citric 0.25 | 0.490 | 4 | plenty | light |
| 3 | 4.061 | 75.0 | Cola Lipid 1.01 | Acetic 0.40 Citric 0.25 | 0 | 4 | plenty | light |
| 4 | 4.022 | 75.0 | SDS 0.196 | $KHCO_3$ 0.231 | 0.501 | 8.5 | plenty | dark |
| 5 | 4.021 | 75.0 | S1210 0.400 | Acetic 0.40 Citric 0.25 | 0 | 4 | much less | light |
| 6 | 4.021 | 75.0 | S1210 0.386 | Acetic 0.40 Citric 0.25 | 0.58 | 4 | much less | light |
| 7 | 4.102 | 75.0 | BTMA 0.23 | Acetic 0.38 Citric 0.24 | 0.59 | 4 | very little | rather dark |

SDS = sodium dodecyl sulfate
BTMA = benzyltrimethylammonium chloride

The results (counted CFUs) after 72 hours on agar were as follows: Sample 1: 15 CFUs after 5 dilutions, 2 CFUs after 6 dilutions; Sample 2: 200 CFUs after 2 dilutions, 12 CFUs after 3 dilutions; Sample 3: 200 CFUs after 2 dilutions, 15 CFUs after 3 dilutions; Sample 4: 36 CFUs after 4 dilutions, 3 CFUs after 5 dilutions; Sample 5: 40 CFUs after 3 dilutions, 3 CFUs after 4 dilutions; Sample 6: 60 CFUs after 3 dilutions, 8 CFUs after 4 dilutions; and Sample 7: 40 CFUs after 3 dilutions, 5 CFUs after 4 dilutions. The final number represents the agar plate still containing CFUs. The next agar plate did not contain any CFUs. For example the difference between sample 2 and 1 is more than two orders of magnitude.

Example 2

The Effect of Various Additives on the Rate of Disintegration of Animal Waste

Materials and devices were as follows:

1. Dog waste collected at the local "Animals in Distress" facility (note: the specimen was refrigerated and replenished every 4 weeks)
2. Sterile Erlenmeyer flasks
3. Balance
4. Magnetic stirrer and bars
5. Deionized water (freshly boiled and cooled to the room temp)

The protocol was as follows:

1. The selected amount of feces was weighed out with the accuracy of 10 mg. All the samples had the same mass within 200 milligrams.
2. Next, the sample was transformed to the Erlenmeyer flask and treated with the selected amount of deionized water (100.0 g) containing either no additives or selected additives.
3. The mixture was mixed at specific rate (about 90 rpm) using a magnetic bar inside the solution and a magnetic stirrer. The amount of time necessary to produce a uniformly distributed suspension was measured.

Table 5 below shows results from a typical disintegration experiment.

TABLE 5

Results from a typical disintegration experiment:

| Mass of waste (g) | Mass of water (g) | Detergent and amount | Time until feces disintegration |
|---|---|---|---|
| 5.03 | 90.0 | none | 16 minutes |
| 5.03 | 90.0 | Tween 80 (non-ionic) - 0.60 g | 2 minutes |
| 4.95 | 90.0 | Triton X100 (non-ionic) - 0.62 g | 4 minutes |
| 4.96 | 90.0 | Sodium dodecyl sulfate (anionic) - 0.14 g | 1 minute |
| 5.01 | 90.0 | Cola lipid (cationic) - 0.59 g | 1 minute |

Example 3

The Effect of Various Additives on the Rate of Malodor Disappearance

Materials and devices were as follows:

1. Dog waste collected at the local "Animals in Distress" facility (note: the specimen was refrigerated and replenished every 4 weeks)
2. Sterile beakers
3. Balance
4. Hot plate, magnetic stirrer and bars
5. Deionized water (freshly boiled and cooled to the room temp)
6. pH-meter The protocol was as follows:

1. The specific amount of feces was weighed (about 4.0 g; accuracy of 1 mg) out and transferred to the 200 mL beaker. The amount of feces did not differ between samples more than 0.20 g.
2. 100.0 g of aqueous solution containing either no additives or the selected ones weighed at the same balance (accuracy of 1 mg) was added to the beaker.
3. The sample was located on a hot plate and stirred magnetically at 40° C. in the fume hood.
4. The samples were checked for the released smell every few minutes.

Typical experiment and results were as follows:

50.0 mL of deionized water containing selected quantities of detergent, pH affecting agent and protease (same concentration as in the formulation divided by 50 since this is the planned dilution with water), pH affecting agent and protease
a. no additives
b. Cola Lipid (0.20 g); protease (Alcalase 3.0T, 0.008 g), sodium perborate tetrahydrate (0.012 g), citric acid (to adjust pH to about 3.0),
c. Cola Lipid (0.20 g); protease (Alcalase 3.0T, 0.008 g), sodium perborate tetrahydrate (0.012 g), sodium hydrogen carbonate (to adjust pH to about 10.0),
d. Cola Lipid (0.20 g); protease (Alcalase 3.0T, 0.008 g), 5% hydrogen peroxide (0.100 g), citric acid (to adjust pH to about 3.0)

was added to 3.00 g of the dog waste. The mixtures were located in the fume hood, heated on the hot plate to 40° C. and stirred magnetically. The malodor of the samples b, c and d disappeared practically instantaneously. The malodor of the sample "a" disappeared after about 30 minutes.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A concentrate composition for sanitizing, disintegrating, and deodorizing solid waste deposited by animals into vegetation comprising a mixture of:
   a) 0.50-50.00% by weight of cocamidopropyl PG-dimonium chloride phosphate,
   b) 0.00-3.00% by weight of at least one enzyme,
   c) 0.00-5.00% by weight an acid,
   d) 0.00-5.00% by weight a colourant,
   e) 0.50-5.00% by weight disodium cocamido-MIPA sulfosuccinate,
   f) 0.00-5.00% by weight an oxidizing agent, and
   g) 27.00-99.00% water.

2. The composition of claim 1, wherein the acid is citric acid.

3. The composition of claim 1, wherein the composition has a pH of less than 7.

4. The composition of claim 1, wherein the oxidizing agent is sodium perborate.

5. A concentrate composition for sanitizing, disintegrating, and deodorizing solid waste deposited by animals into vegetation comprising a mixture of:
   a) 15.00-25.00% by weight of cocamidopropyl PG-dimonium chloride phosphate,
   b) 0.80-1.00% by weight of a protease,
   c) 0.20-1.00% by weight of an amylase,
   d) 0.10-0.20% by weight an acid,
   e) 0.01-1.00% by weight a colourant,
   f) 0.50-1.00% by weight disodium cocamido-MIPA sulfosuccinate,
   g) 0.10-0.50% by weight an oxidizing agent, and
   h) 70.30-83.29% by weight water.

6. The composition of claim 5, wherein the acid is citric acid.

7. The composition of claim 5, wherein the composition has a pH of less than 7.

8. The composition of claim 5, wherein the oxidizing agent is sodium perborate.

9. A concentrate composition for sanitizing, disintegrating, and deodorizing solid waste deposited by animals into vegetation comprising a mixture of:
   a) 19.50% by weight of cocamidopropyl PG-dimonium chloride phosphate,
   b) 0.80% by weight of a protease,
   c) 0.20% by weight of an amylase,
   d) 0.15% by weight an acid,
   e) 0.01% by weight a colourant,
   f) 0.50% by weight disodium cocamido-MIPA sulfosuccinate,
   g) 0.30% by weight an oxidizing agent, and
   h) 78.54% by weight water.

10. The composition of claim 9, wherein the acid is citric acid.

11. The composition of claim 9, wherein the composition has a pH of less than 7.

12. The composition of claim 9, wherein the oxidizing agent is sodium perborate.

* * * * *